US006630451B1

(12) United States Patent
Zhang et al.

(10) Patent No.: US 6,630,451 B1
(45) Date of Patent: Oct. 7, 2003

(54) BENZIMIDAZOLONE PEPTIDOMETICS AS THROMBIN RECEPTOR ANTAGONIST

(75) Inventors: Han-Cheng Zhang, Lansdale, PA (US); Bruce E. Maryanoff, Forest Grove, PA (US); David F. McComsey, Warminster, PA (US); Kimberly B. White, North Wales, PA (US)

(73) Assignee: OrthoMcNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/599,826

(22) Filed: Jun. 22, 2000

Related U.S. Application Data

(60) Provisional application No. 60/141,552, filed on Jun. 29, 1999.

(51) Int. Cl.$^7$ ................................................. C07K 5/06
(52) U.S. Cl. ........................ 514/19; 514/385; 514/386; 514/387; 514/393; 514/394; 548/300; 548/305; 546/273.4
(58) Field of Search .......................... 514/19, 385, 386, 514/387, 393, 394; 548/300, 305; 546/273.4

(56) References Cited

U.S. PATENT DOCUMENTS

| 4,977,153 A | 3/1991 | Louis et al. ............. 514/237.5 |
| 5,439,906 A | 8/1995 | Bock et al. .................. 514/220 |
| 5,530,026 A | 6/1996 | Gaudreault et al. ......... 514/524 |
| 6,017,890 A | 1/2000 | Hoekstra et al. .............. 514/19 |

FOREIGN PATENT DOCUMENTS

| CA | 2011222 A1 | 9/1990 |
| EP | 0 385 850 A1 | 2/1990 |
| JP | WO 99/00357 A1 | 1/1999 |
| WO | WO 92/14750 A1 | 9/1992 |
| WO | WO 93/18026 A1 | 9/1993 |
| WO | WO 99/33798 A1 | 7/1999 |
| WO | WO 99/42475 A1 | 8/1999 |

OTHER PUBLICATIONS

"Thrombin–Induced Events in Non–Platelet Cells Are Mediated by the Unique Proteolytic Mechanism Established for Yhe Cloned Platelet Thrombin Receptor", David T. Hung, et al., The Journal of Cell Biology, vol. 116, No. 3, Feb. 1992, pp. 827–832.
Thrombin Receptor Activation Causeds Rapid Neural Cell Rounding and Neurite Retraction Independent of Classic Second Messengers, Kees Jalink et al., The Journal of Cell Biology, vol. 118, No. 2, Jul. 1992, pp. 411–419.
Thrombin–Induced Expression of Endothelial P–Selectin and Intercellular Adhesion Moleculte–1: A Mechanism for Stabilizing Neutrophil Adhesion, Yasuo Sugama et al., The Journal of Cell Biology, vol. 119, No. 4, Nov. 1992, pp. 935–944.

Molecular Cloning of a Functional Thrombin Receptor Reveals a Novel Proteolytic Mechanism of Receptor Activation, Thien–kHAL h. vU Et Al., cELL, vol. 64, Mar. 1991, pp. 1057–1068.
"Thrombin Effects on Osteoblastic Cells—II. Structure––Function Relationships" Dimitris N. Tatakis et al., Biochemical and Biophysical Research Communications, vol. 174, No. 1, Jan. 1991, pp. 181–188.
"Thrombin Induces Release of Platelet–Derived Growth Factor–Like Molecule(S) by Cultured Human Endothelial Cells", John M. Harlan et al., The Journal of Cell Biology, vol. 103, Sep. 1986, pp. 1129–1133.
"Endothelial Leukocyte Adhesion Molecule 1: An Inducible Receptor for Neutrophils Related to Complement Regulatory Proteins and Lectins", Michael P. Bevilacqua et al., Science, vol. 243, Mar. 1989, pp. 1160–1164.
"Enhancement of Incisional Wound Healing and Neovascularization in Normal Rats by Thrombin and Synthetic Thrombin Receptor–Activating Peptides", D.H. Carney et al., The American Society for Clinical Investigation, Inc., vol. 89, May 1992, pp. 1469–1477.
"Cloning and Characterization of Human Protease–Activated Receptor 4", Wen–Feng Xu et al., Proc. Natl. Acad. Sci. USA, vol. 95, Jun. 1998, pp. 6642–6646.
"Molecular Cloning of a Potential Proteinase Activated Receptor", Sverker Nystedt et al., Proc. Natl. Acad. Sci. USA, vol. 91, Sep. 1994, pp. 9208–9212.
"Thrombin–Induced Events in Non–Platelet Cells are Mediated by the Unique Proteolytic Mechanism Established for the Cloned Platelet Thrombin Receptor", David T. Hung, et al., The Journal of Cell Biology, vol. 116, No. 3, Feb. 1992, pp. 827–832.
Thrombin Receptor Activation Causes Rapid Neural Cell Rounding and Neurite Retraction Independent of Classic Second Messengers, Kees Jalink et al., The Journal of Cell Biology, vol. 118, No. 2, Jul. 1992, pp. 411–419.
"Thrombin–Induced Expression of Endothelial P–Selectin and Intercellular Adhesion Molecule–1: A Mechanism for Stabilizing Neutrophil Adhesion", Yasuo Sugama et al., The Journal of Cell Biology, vol. 119, No. 4, Nov. 1992, pp. 935–944.
"Molecular Cloning of a Functional Thrombin Receptor Reveals a Novel Proteolytic Mechanism of Receptor Activation", Thien–Khal H. Vu et al., Cell, vol. 64, Mar. 1991, pp. 1057–1068.

(List continued on next page.)

Primary Examiner—Christopher S. F. Low
Assistant Examiner—David Lukton

(57) ABSTRACT

The invention is directed to novel benzimidazolone peptidomimetic compounds which are useful as thrombin receptor antagonists for the treatment of diseases associated with thrombosis, restenosis, hypertension, heart failure, arrhythmia, inflammation, angina, stroke, atherosclerosis, ischemic conditions, Angiogenesis related disorders, cancer, and neurodegenerative disorders. Pharmaceutical compositions comprising the substituted benzimidazolone peptidomimetics of the present invention and methods of treating conditions mediated by the thrombin receptor are also disclosed.

10 Claims, No Drawings

OTHER PUBLICATIONS

"Response of a Human Megakaryocytic Cell Line to Thrombin: Increase in Intracellular Free Calcium and Mitogen Release", Cindy L. A. Jones, et al., Biochemica et Biophysica Acta. 1136, 1992, pp. 272–282.

"Condensed Heteroaromatic Ring Systems—XIII. One–Step Synthesis of 2–Substituted 1–Methylsulfoonylindoles from N–(2–Halophenyl) Methanesulfonamides", Takao Sakamoto et al., Chem. Pharm. Bull., No. 4, Sep. 1987, pp. 1305–1308.

"An Antibody Against the Exosite of the Cloned Thrombin Receptor Inhibits Experimental Arterial Thrombosis in the African Green Monkey", Jacquelynn J. Cook et al., Basic Science Reports, Oct. 1994, pp. 2961–2971.

"Protease–Activated Receptor 3 is a Second Thrombin Receptor in Humans", Hiroaki Ishihara, Nature, vol. 386, Apr. 1997, pp. 502–508.

"Heterocycle–Peptide Hybrid Compounds, Aminotriazole–Containing Agonists of the Thrombin Receptor (PAR–1)", David F. McComsey et al., Bioorganic & Medicinal Chemistry Letters 9 (1999), pp. 1423–1428.

"Design, Synthesis, and Biological Characterization of a Peptide–Mimetic Antagonist for a Tethered–Ligand Receptor" Patricia Andrade–Gordon et al., PNAS, vol. 96, No. 22, Oct. 26, 1999, pp. 12257–12262.

Thrombin Receptor (PAR–1) Antagoonists, Heterocycle–Based Peptidomimetics of the SFLLR Agonist MOTIF, William J. Hoekstra et al., Bioorganic & Medicinal Chemistry Letters 8, (1998), pp. 1649–1654.

"Development of Potent Thrombin Receptor Antagonist Peptides", Michael S. Bernatowicz et al., J. Med. Chem., 1996, vol. 39, No. 25, pp. 4879–4887.

"Design, Synthesis, and Structure–Activity Relationship for a Series of Factor XA Inhibitors Containing the Benzimidazoone Nucleus as a Central Template", Charles K. Marlowe et al., Medicinal Chemistry, COR Therapeutics, Inc., Abstract.

"Novel Indole–Based Peptidomimetics as Potent Thrombin Receptor (PAR–1) Antagonists", Han Cheng Zhang et al., The R.W. Johnson Pharmaceutical Research Institute, Abstract.

"Approaches to the Synthesis of Ureapeptoid Peptidomimetics" John A. W. Kruijtzer et al., Tetraehedron Letters, vol. 38, No. 30, pp. 5335–5338, 1997.

U.S. patent application Ser. No. 09/603,229, McComsey et al.

U.S. patent application Ser. No. 09/603,231, Zhang et al.

U.S. patent application Ser. No. 09/603,338, Zhang et al.

BENZIMIDAZOLONE PEPTIDOMETICS AS THROMBIN RECEPTOR ANTAGONIST

This patent application claims priority from provisional patent application Ser. No. 60/141,552, which was filed Jun. 29, 1999. This invention relates to certain novel thrombin receptor antagonists, their synthesis and their use for the treatment of diseases associated with thrombosis, restenosis, hypertension, heart failure, arrhythmia, inflammation, angina, stroke, atherosclerosis, ischemic conditions, Angiogenesis related disorders, cancer, and neurodegenerative disorders.

FIELD OF THE INVENTION

BACKGROUND OF THE INVENTION

Thrombin is an important serine protease in hemostasis and thrombosis. One of the key actions of thrombin is cellular modulation via receptor activation. A functional human thrombin receptor (PAR-1), cloned by Coughlin in 1991 (T. -K. Vu, Cell 1991, 64, 1057), was found to be a member of the G-protein coupled receptor (GPCR) superfamily. The receptor activation putatively occurs by N-terminal recognition and proteolytic cleavage at the Arg-41/Ser-42 peptide bond to reveal a truncated N-terminus. This new N-terminus acting as a tethered ligand to recognize a site on the receptor, can trigger activation and signal transduction leading to platelet aggregation. Since 1991, three other protease-activated receptors with extensive homology to the thrombin receptor, "PAR-2" (S. Nystedt, Proc. Natl. Acad. Sci USA 1994, 91, 9208), "PAR-3" (H. Ishihara, Nature 1997, 386, 502), and "PAR-4" (W.-F. Xu, Proc. Natl. Acad. Sci USA 1998, 95, 6642), have been cloned. Thrombin receptor (PAR-1) specific antibody-induced blockade of the platelet thrombin receptor has shown efficacy against arterial thrombosis in vivo (J. J. Cook Circulation 1995, 91, 2961). Hence, antagonists of the thrombin receptor (PAR-1) are useful to block these protease-activated receptors and, as such, may be used to treat platelet mediated thrombotic disorders such as myocardial infarction, stroke, restenosis, angina, atherosclerosis, and ischemic conditions.

The thrombin receptor (PAR-1) has also been identified on other cell types: endothelial, fibroblast, renal, osteosarcoma, smooth muscle, myocytes, tumor, and neuronal/glia. Thrombin activation of endothelial cells upregulates P-selectin to induce polymorphonuclear leukocyte adhesion—an inflammatory response of the vessel wall (Y. Sugama, J. Cell Biol. 1992, 119, 935). In fibroblasts, thrombin receptor (PAR-1) activation induces proliferation and transmission of mitogenic signals (D. T. Hung, J. Cell Biol. 1992, 116, 827). Thrombin has been implicated in osteoblast proliferation through its activation of osteoblast cells (D. N. Tatakis, Biochem. Biophys. Res. Commun. 1991, 174, 181). Thrombin has been implicated in the regulation and retraction of neurons (K. Jalink, J. Cell. Biol. 1992, 118, 411). Therefore, in this context, the antagonist compounds of this invention may also be useful against inflammation, osteoporosis, Angiogenesis related disorders, cancer, neurodegenerative disorders, hypertension, heart failure, arrhythmia, glomerulonephritis.

The compounds of the present invention are a structurally novel class of benzimidazolone peptidomimetics represented by the general formula (I) below.

SUMMARY OF THE INVENTION

The present invention is directed to structurally novel compounds represented by the following general formula (I):

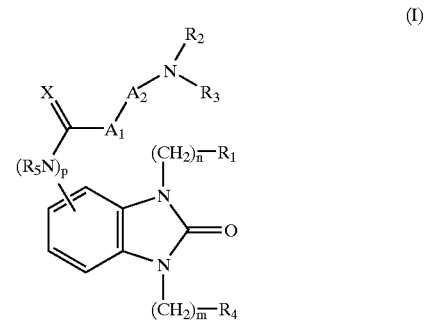

wherein $A_1$ and $A_2$ are each independently a D- or L-amino acid selected from the group consisting of alanine, β-alanine, arginine, homoarginine, cyclohexylalanine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3 diaminopropionic acid (optionally substituted with acyl, $C_1$–$C_4$ alkyl, aroyl, amidino, or MeC(NH)—), glutamine, glycine, indanylglycine, lysine (optionally substituted with acyl, $C_1$–$C_4$ alkyl, aroyl, MeC(NH)—), valine, methionine, proline, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), tetrahydroisoquinoline-3-COOH, threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

Preferably, $A_1$ and $A_2$ are each independently an L-amino acid selected from the group consisting of alanine, β-alanine, arginine, homoarginine, cyclohexylalanine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3 diaminopropionic acid (optionally substituted with acyl, $C_1$–$C_4$ alkyl, aroyl, amidino, or MeC(NH)—), glutamine, glycine, indanylglycine, lysine (optionally substituted with acyl, $C_1$–$C_4$ alkyl, aroyl, MeC(NH)—), valine, methionine, proline, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), tetrahydroisoquinoline-3-COOH, threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein the substituents on the aromatic amino acid are independently selected from one or more of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

- $R_1$ is selected from amino, $C_1$–$C_8$ alkylamino, $C_1$–$C_8$ dialkylamino, arylamino, ar$C_1$–$C_8$ alkylamino, $C_3$–$C_8$ cycloalkylamino, heteroalkyl$C_1$–$C_8$ alkylamino, heteroalkyl$C_1$–$C_8$ alkyl-N-methylamino, $C_1$–$C_8$ dialkylamino$C_1$–$C_8$ alkylamino, —N($C_1$–$C_8$alkyl)—$C_1$–$C_8$ alkyl-N($C_1$–$C_8$alkyl)$_2$, N($C_1$–$C_8$ alkyl)($C_1$–$C_8$ alkenyl), —N($C_1$–$C_8$alkyl)($C_3$–$C_8$cycloalkyl), heteroalkyl or substituted heteroalkyl wherein the substituent on the heteroalkyl is selected from oxo, amino, $C_1$–$C_8$ alkoxy$C_1$–$C_8$ alkyl, $C_1$–$C_8$ alkylamino or $C_1$–$C_8$ dialkylamino;

- Preferably, $R_1$ is selected from amino, $C_1$–$C_6$ alkylamino, $C_1$–$C_6$ dialkylamino, arylamino, ar$C_1$–$C_6$ alkylamino, heteroalkyl$C_1$–$C_6$ alkylamino, —N($C_1$–$C_6$alkyl)—$C_1$–$C_6$alkyl-N($C_1$–$C_6$alkyl)$_2$, heteroalkyl or substituted heteroalkyl wherein the substituent on the heteroalkyl is selected from oxo, amino, $C_1$–$C_6$alkoxy$C_1$–$C_6$ alkyl, $C_1$–$C_6$ alkylamino or $C_1$–$C_6$ dialkylamino;

- $R_2$ and $R_3$ are each independently selected from hydrogen, $C_1$–$C_8$ alkyl, $C_3$–$C_8$ cycloalkyl, $C_3$–$C_8$ cycloalkyl$C_1$–$C_8$ alkyl, aryl, heteroalkyl, substituted heteroalkyl (wherein the substituent on the heteroalkyl is one or more substituents independently selected from $C_1$–$C_8$ alkoxycarbonyl, $C_1$–$C_8$ alkyl, or $C_1$–$C_4$ alkylcarbonyl), heteroalkyl$C_1$–$C_8$ alkyl, indanyl, acetamidino$C_1$–$C_8$ alkyl, amino$C_1$–$C_8$ alkyl, $C_1$–$C_8$ alkylamino$C_1$–$C_8$ alkyl, $C_1$–$C_8$, dialkylamino$C_1$–$C_8$ alkyl, unsubstituted or substituted heteroaryl$C_1$–$C_8$ alkyl or unsubstituted or substituted ar$C_1$–$C_8$ alkyl, wherein the substituent on the aralkyl or heteroarylalkyl group is one or more substituents independently selected from halogen, nitro, amino, $C_1$–$C_8$ alkyl, $C_1$–$C_8$ alkoxy, hydroxy, cyano, $C_1$–$C_4$ alkylcarbonyl, $C_1$–$C_8$ alkoxycarbonyl, hydroxy$C_1$–$C_8$ alkyl or aminosulfonyl; or

- $R_2$ and $R_3$ together with the nitrogen to which they are attached, alternatively form an unsubstituted or substituted heteroalkyl group selected from piperidinyl, piperazinyl, morpholinyl or pyrrolidinyl, wherein the substituent is one or more substituents independently selected from $C_1$–$C_8$ alkyl $C_1$–$C_8$ alkoxycarbonyl or $C_1$–$C_4$ alkylcarbonyl;

- Preferably, $R_2$ is selected from hydrogen or $C_1$–$C_6$ alkyl;
- $R_3$ is selected from $C_1$–$C_8$ alkyl, $C_3$–$C_6$ cycloalkyl, $C_3$–$C_6$ cycloalkyl$C_1$–$C_6$ alkyl, aryl, heteroaryl$C_1$–$C_6$ alkyl, substituted heteroaryl$C_1$–$C_6$ alkyl wherein the substituent is $C_1$–$C_4$ alkyl, heteroalkyl, heteroalkyl$C_1$–$C_6$ alkyl, indanyl, acetamidino$C_1$–$C_6$ alkyl, amino$C_1$–$C_6$ alkyl, $C_1$–$C_6$ alkylamino$C_1$–$C_6$ alkyl, $C_1$–$C_6$ dialkylamino$C_1$–$C_6$ alkyl, ar$C_1$–$C_8$ alkyl, substituted ar$C_1$–$C_8$ alkyl wherein the substituent on the aralkyl group is one to five substituents independently selected from halogen, nitro, amino, $C_1$–$C_6$ alkyl, $C_1$–$C_6$ alkoxy, $C_1$–$C_6$ alkoxycarbonyl, hydroxyalkyl or aminosulfonyl; or

- $R_2$ and $R_3$, together with the nitrogen to which they are attached, alternatively form an unsubstituted or substituted heteroalkyl group selected from piperidinyl, piperazinyl or pyrrolidinyl, wherein the substituent is independently one or two substituents selected from $C_1$–$C_6$ alkyl;

- $R_4$ is selected from unsubstituted or substituted aryl, ar$C_1$–$C_8$ alkyl, $C_3$–$C_8$ cycloalkyl, or heteroaryl, where the substituents on the aryl, ar$C_1$–$C_8$ alkyl, cycloalkyl or heteroaryl group are independently selected from one or more of halogen, nitro, amino, cyano, hydroxyalkyl, $C_1$–$C_8$ alkyl, $C_1$–$C_8$ alkoxy, hydroxy, $C_1$–$C_4$ alkylcarbonyl, $C_1$–$C_8$ alkoxycarbonyl, fluorinated $C_1$–$C_4$ alkyl, fluorinated $C_1$–$C_4$ alkoxy or $C_1$–$C_4$ alkylsulfonyl;

- Preferably, $R_4$ is selected from unsubstituted or substituted aryl, ar$C_1$–$C_6$ alkyl, $C_3$–$C_6$ cycloalkyl or heteroaryl, where the substituents on the aryl, aralkyl, cycloalkyl or heteroaryl group are independently selected from one to three substituents selected from halogen, cyano, $C_1$–$C_4$ alkyl, $C_1$–$C_4$ alkoxy, $C_1$–$C_4$ alkoxycarbonyl, fluorinated $C_1$–$C_4$ alkyl, fluorinated $C_1$–$C_4$ alkoxy or $C_1$–$C_4$ alkylsulfonyl;

- $R_5$ is selected from hydrogen or $C_1$–$C_8$ alkyl; preferably, $R_5$ is hydrogen;

- X is oxygen or sulfur; preferably, X is oxygen;
- m is an integer selected from 0, 1, 2 or 3;
- n is an integer selected from 2 or 3; and
- p is an integer selected from 0 or 1; preferably, p is 1;

and pharmaceutically acceptable salts thereof.

In a preferred embodiment of the present invention:

$A_1$ is an L-amino acid selected from the group consisting of alanine, arginine, cyclohexylalanine, glycine, proline, tetrahydroisoquinoline-3-COOH, and an unsubstituted or substituted aromatic amino acid selected from the group consisting of phenylalanine, naphthylalanine, homophenylalanine, and O-methyl tyrosine, wherein the substituents on the aromatic amino acid are independently selected from one to five of (preferably, one to three of) halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$A_2$ is an L-amino acid selected from the group consisting of alanine, β-alanine, arginine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, lysine (optionally substituted with acyl, $C_1$–$C_4$ alkyl, aroyl, MeC (NH)—), valine, methionine, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, and histidine, wherein the substituents on the aromatic amino acid are independently selected from one to five of (preferably, one to three of) halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_2$ is selected from hydrogen or $C_1$–$C_4$ alkyl;

m is 1 and n is 2;

and all other variables are as defined previously;

and pharmaceutically acceptable salts thereof.

In a class of the invention:

$A_1$ is an L-amino acid selected from the group consisting of alanine, arginine, cyclohexylalanine, glycine, proline, and an unsubstituted or substituted aromatic amino acid selected from the group consisting of phenylalanine, naphthylalanine, homophenylalanine, and O-methyl tyrosine, wherein the substituents on the aromatic amino acid are independently one to two substituents selected from halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$A_2$ is an L-amino acid selected from the group consisting of alanine, β-alanine, arginine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, lysine (optionally substituted with acyl, $C_1$–$C_4$ alkyl, aroyl, MeC(NH)—), valine, methionine, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, MeC(NH)—), and an unsubstituted or substituted aromatic amino acid selected from the group consisting of phenylalanine, heteroarylalanine, and histidine, wherein the substituents on the aromatic amino acid are independently one to two substituents selected from halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, or nitro;

$R_1$ is selected from dimethylamino, diethylamino, di-(n-propyl)amino,

Preferably, $R_1$ is:

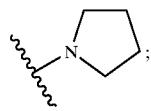

$R_2$ is selected from hydrogen, methyl or ethyl;

$R_3$ is selected from 2-indanyl, phenyl, cyclohexylmethyl, cyclopentyl, pyridylmethyl, furanylmethyl, 2-(4-methylfuranyl)methyl, thienylmethyl, diphenylmethyl, 4-imidazolylethyl, 2-(4-N-methyl)imidazolylethyl, n-octyl, phenyl-n-propyl, aminoethyl, aminopropyl, amino-n-pentyl, dimethylaminoethyl, 4-aminophenylsulfonylaminomethyl, acetamidinylethyl, 2-N-pyrrolidinylethyl, N-ethoxycarbonylpiperidinyl, unsubstituted or substituted phenylethyl or unsubstituted or substituted benzyl wherein the substituents on the phenylethyl or benzyl are independently one or two substituents selected from methyl, fluorine, chlorine, nitro, methoxy, methoxycarbonyl or hydroxymethyl; or $R_2$ and $R_3$, together with the nitrogen to which they are attached, alternatively form a heteroalkyl group selected from piperidinyl, or 4-(N-methyl)piperazinyl;

$R_4$ is selected from cyclohexyl, 2-naphthyl, phenylethyl, 4-fluorophenylethyl, or unsubstituted or substituted phenyl, where the substituents on the phenyl are independently selected from one to two substituents selected from fluorine, chlorine, iodine, methyl, cyano, or trifluoromethyl;

Preferably, $R_4$ is 2,6-dichlorophenyl or 2-methylphenyl;

and all other variables are as defined previously;

and pharmaceutically acceptable salts thereof.

In a subclass of the invention, $A_1$ is selected from 3,4-Difluorophenylalanine or 4-Chlorophenylalanine;

$A_2$ is selected from 2,4-Diaminobutyric acid or 4-Pyridylalanine;

$R_2$ is hydrogen;

$R_3$ is selected from benzyl or 2-aminoethyl;

and all other variables are as defined previously;

and pharmaceutically acceptable salts thereof.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An example of the invention is a method of treating a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, atherosclerosis, ischemic conditions, hypertension, heart failure, arrhythmia, glomerulonephritis, osteoporosis, Angiogenesis related disorders, cancer, neurodegenerative disorders and a variety of vaso-occlusive disorders in a subject in need thereof comprising administering to the subject a therapeutically effective amount of any of the compounds or pharmaceutical compositions described above. In a preferred embodiment, the therapeutically effective amount of the compound is from about 0.1 mg/kg/day to about 300 mg/kg/day.

Also included in the invention is the use of any of the compounds described above for the preparation of a medicament for a disorder (preferably, a platelet-mediated thrombotic disorder) selected from arterial and/or venous thrombosis, acute myocardial infarction, reocclusion following thrombolytic therapy and/or angioplasty, inflammation, unstable angina, stroke, restenosis, atherosclerosis, ischemic conditions, hypertension, heart failure, arrhythmia, glomerulonephritis, osteoporosis, Angiogenesis related disorders, cancer, neurodegenerative disorders or a variety of vaso-occlusive disorders in a subject in need thereof.

DETAILED DESCRIPTION OF THE INVENTION

More particularly, the present invention is directed to compounds of the following formula (I):

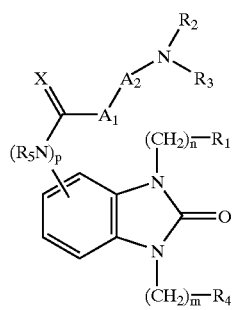

(I)

wherein $A_1$, $A_2$, $R_1$, $R_2$, $R_3$, $R_4$, $R_5$, X, m, n and p are as previously defined. In a particularly preferred embodiment, the compounds have the formula

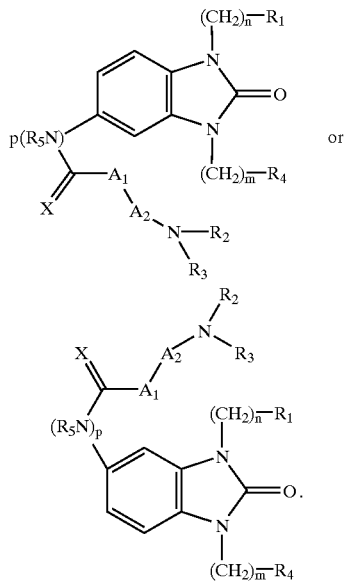

The compounds of the present invention are thrombin receptor antagonists and as such are useful in treating thrombosis, restenosis, hypertension, heart failure, arrhythmia, myocardial infarction, glomerulonephritis, reocclusion following thrombolytic therapy, reocclusion following angioplasty, inflammation, angina, stroke, atherosclerosis, ischemic conditions, a vaso-occlusive disorder, neurodegenerative disorders, Angiogenesis related disorders and cancer. These compounds are also useful as antithrombotics in conjunction with fibrinolytic therapy (e.g., t-PA or streptokinase).

In the compounds of formula (I), the amino acid residues comprising the $A_1$ and $A_2$ substituents are attached to the adjacent moiety according to standard nomenclature so that the amino-terminus (N-terminus) of the amino acid is drawn on the left and the carboxy-terminus of the amino acid is drawn on the right. So, for example, in Compound 1 in Table 1, where $A_1$ is 3,4-difluorophenylalanine and $A_2$ is Dbu (2,4-Diaminobutyric acid), the N-terminus of the 3,4-difluorophenylalanine ($A_1$) is attached to the carbonylgroup and the carboxy-terminus of the 3,4-difluorophenylalanine ($A_1$) is attached to the N-terminus of the $A_2$ substituent (Dbu), similarly, the N-terminus of the Dbu ($A_2$) is attached to the carboxy-terminus of the $A_1$ substituent and the carboxy-terminus of the Dbu ($A_2$) is attached to the N—$R_2R_3$ group.

When a particular group is "substituted" (e.g., Phe, aryl, heteroalkyl, heteroaryl), that group may have one or more substituents, preferably from one to five substituents, more preferably from one to three substituents, most preferably from one to two substituents, independently selected from the list of substituents.

Under standard nomenclature used throughout this disclosure, the terminal portion of the designated side chain is described first, followed by the adjacent functionality toward the point of attachment. Thus, for example, a "phenyl$C_1$–$C_6$ alkylamido$C_1$–$C_6$alkyl" substituent refers to a group of the formula

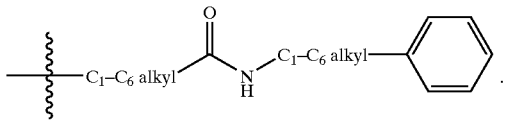

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted alkyl and alkoxy whether used alone or as part of a substituent group, include straight and branched chains having 1 to 8 carbon atoms, or any number within this range. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 carbons. Similarly, alkenyl and alkynyl groups include straight and branched chain alkenes and alkynes having 1 to 8 carbon atoms, or any number within this range.

The term "aryl" as used herein refers to an unsubstituted or substituted aromatic group such as phenyl and naphthyl. The term "aroyl" refers to the group —C(O)-aryl.

The term "heteroalkyl" as used herein represents an unsubstituted or substituted stable three to seven membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heteroalkyl group may be attached at any heteroatom or carbon atom which results in the creation of a stable structure. Examples of such heteroalkyl groups include, but are not limited to azetidinyl, piperidinyl, pyrrolidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl. Preferred heteroalkyl groups include pyrrolidinyl, piperidinyl, piperazinyl, morpholinyl, azetidinyl and tetrahydrothiazolyl.

The term "heteroaryl" as used herein represents an unsubstituted or substituted stable five or six membered monocyclic aromatic ring system or an unsubstituted or substituted nine or ten membered benzo-fused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom that results in the creation of a stable structure. Examples of heteroaryl groups include, but are not limited to pyridyl, pyridazinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl adeninyl or quinolinyl. Prefered heteroaryl groups include pyridyl, pyrrolyl, pyrazinyl, thiadiazolyl, pyrazolyl, thienyl, triazolyl and quinolinyl.

The term "aralkyl" means an alkyl group substituted with one, two or three aryl groups (e.g., benzyl, phenylethyl, diphenylmethyl, triphenylmethyl). Similarly, the term "aralkoxy" indicates an alkoxy group substituted with an aryl group (e.g., benzyloxy). The term aminoalkyl refers to an alkyl group substituted with an amino group (i.e., -alkyl-$NH_2$). The term "alkylamino" refers to an amino group substituted with an alkyl group (i.e., —NH-alkyl). The term "dialkylamino" refers to an amino group which is disubstituted with alkyl groups wherein the alkyl groups can be the same or different (i.e., —N-[alkyl]$_2$).

The term "acyl" as used herein means an organic radical having 1 to 6 carbon atoms (branched or straight chain) derived from an organic acid by removal of the hydroxyl group.

The term "oxo" refers to the group =O.

The term "carbonyl" refers to the group C(O).

The term "halogen" shall include iodine, bromine, chlorine and fluorine.

The term "$N(CH_2)_4$" as used herein (e.g., in the Tables), refers to a pyrrolidinyl group having the structure

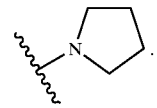

Similarly, "$N(CH_2)_5$", "$N(CH_2)_3$", "$NCH_2S(CH_2)_2$" and "$N(CH_2)_2O(CH_2)_2$" refer to

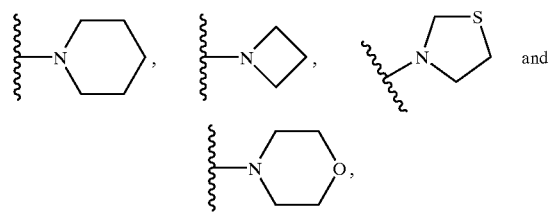

respectively.

Similarly "$C_6H_{11}$" and "$C_5H_9$" (or "c-$C_6H_{11}$" and "c-$C_5H_9$") refer to cyclohexyl and cyclopentyl groups, respectively.

Whenever the term "alkyl" or "aryl" or either of their prefix roots appear in a name of a substituent (e.g., aralkyl, dialkylamino) it shall be interpreted as including those limitations given above for "alkyl" and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

As used herein, the term "phosgene equivalent" represents the class of carbonic acid derivatives which include 4-nitrophenyl chloroformate, phosgene or "$COCl_2$," phenyl chloroformate, triphosgene or "$(CCl_3O)_2CO$," carbonyldiimidazole, diethyl carbonate or diphenyl carbonate.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "composition" is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention.

Particularly preferred compounds of the present invention and their biological data are shown in Tables 1 and 2, following; the amino acids bear the "L" absolute configuration unless denoted otherwise. The Tables contain $IC_{50}$ values ($\mu$M) of the compounds in a thrombin receptor binding assay, and $IC_{50}$ values ($\mu$M) against platelet aggregation stimulated by thrombin.

aminobenzimidazolone intermediate AAG4 with a dipeptide amine AAG6 via a urea linkage as described in the general Scheme AAGeneric. The appropriately nitro substituted benzimidazolone AAG1 (Scheme AAGeneric) was alkylated with a substituted aralkyl or heteroaryl alkyl halide and a base such as sodium hydride in a dipolar aprotic solvent such as DMF to give AAG2 as a mixture of two regioisomers. Two isomers were separated by silica gel column and then alkylated, with an aminoalkyl halide and a base such as

TABLE 1

6-Substituted Benzimidazolone Peptidomimetics

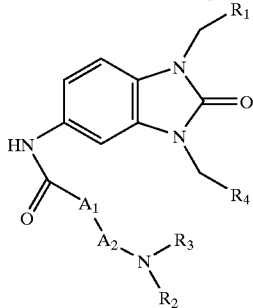

| Compd | $R_1$ | $R_4$ | $A_1$ | $A_2NR_2R_3$ | Thr GFP Aggr[a] | Thr Recptr Bdg[b] |
|---|---|---|---|---|---|---|
| 1 | $CH_2N(CH_2)_4$ | 2,6-DiCl—Ph[c] | 3,4-DiF—Phe[d] | Dbu[e]—NHBn | 0.39 | 1.6 |
| 4 | $CH_2NMe_2$ | 2-Me—Ph | 3,4-DiF—Phe | Dbu—NHBn | 0.23 | 0.7 |
| 5 | $CH_2N(CH_2)_4$ | 2-Me—Ph | 3,4-DiF—Phe | Dbu—NHBn | 0.28 | 0.4 |
| 6 | $CH_2N(CH_2)_4$ | 4-F—Ph | 3,4-DiF—Phe | Dbu—NHBn | 6 | 0.6 |
| 8 | $CH_2N(CH_2)_4$ | 4-F—Ph | 3,4-DiF—Phe | 4-PyrAla[f]—NH(CH$_2$)$_2$NH$_2$ | 5.8 | 0.5 |

TABLE 2

5-Substituted Benzimidazolone Peptidomimetics

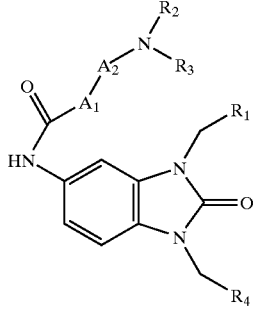

| Compd | $R_1$ | $R_4$ | $A_1$ | $A_2NR_2R_3$ | Thr GFP Aggr[a] | Thr Recptr Bdg[b] |
|---|---|---|---|---|---|---|
| 2 | $CH_2N(CH_2)_4$ | 2-Me—Ph | 3,4-DiF—Phe | Dbu—NHBn | 7 | 3 |
| 3 | $CH_2NMe_2$ | 2-Me—Ph | 3,4-DiF—Phe | Dbu—NHBn | 7.7 | 1.9 |
| 7 | $CH_2N(CH_2)_4$ | 2,6-DiCl—Ph | 3,4-DiF—Phe | Dbu—NHBn | 5.5 | 1.7 |

[a]Thrombin-induced gel-filtered platelet aggregation assay.
[b]Thrombin receptor (PAR-1) binding assay.
[c]2,6-Dichlorophenyl.
[d]3,4-Difluorophenylalanine.
[e]2,4-Diaminobutyric acid.
[f]4-Pyridylalanine.

The antagonists of the present invention may be prepared via a convergent solution-phase synthesis by coupling an sodium hydride in a dipolar aprotic solvent such as DMF to give two regioisomers AAG3, respectively. Reduction of nitro group in AAG3 in a classical manner with for example iron and acetic acid or with a newer method such as dimethyl hydrazine and iron to gave aminobenzimidazolone intermediate AAG4.

Dipeptide amine AAG6 can be synthesized from the corresponding protected amino acids using standard peptide coupling conditions. Thus, an Fmoc protected amino-acid (A$_2$) AAG5 (Scheme AAGeneric) was coupled to amine R$_2$R$_3$NH using a coupling agent, such as dicyclohexylcarbodiimide (DCC) or diisopropylcarbodiimide (DIC) and 1-hydroxybenzotriazole (HOBT) in a dipolar aprotic solvent such as DMF to give the amide. The amide was then Fmoc deprotected with a dialkylamine in a dipolar aprotic solvent, such as diethylamine in acetonitrile. The resulting amine was coupled to the second Fmoc protected amino-acid (A$_1$) in the same way with a coupling agent, such as DIC and HOBT in a dipolar aprotic solvent such as DMF to give the dipeptide. The dipeptide was then Fmoc deprotected as above with a dialkylamine in a dipolar aprotic solvent such as acetonitrile to afford dipeptide amine AAG6.

Aminobenzimidazolone intermediate AAG4 was treated with a phosgene equivalent such as 4-nitrophenyl chloroformate, phosgene or "COCl$_2$," phenyl chloroformate, triphosgene or "(CCl$_3$O)$_2$CO," carbonyldiimidazole, diethyl carbonate or diphenyl carbonate.and a base such as diisopropylethylamine in a solvent such as dichloromethane, and to this was then added dipeptide amine AAG6 to give a urea. Removal of the protecting group, if necessary, such as the Boc group with an acid such as trifluoroacetic acid from the side chain of dipeptide afforded final targets AAG7.

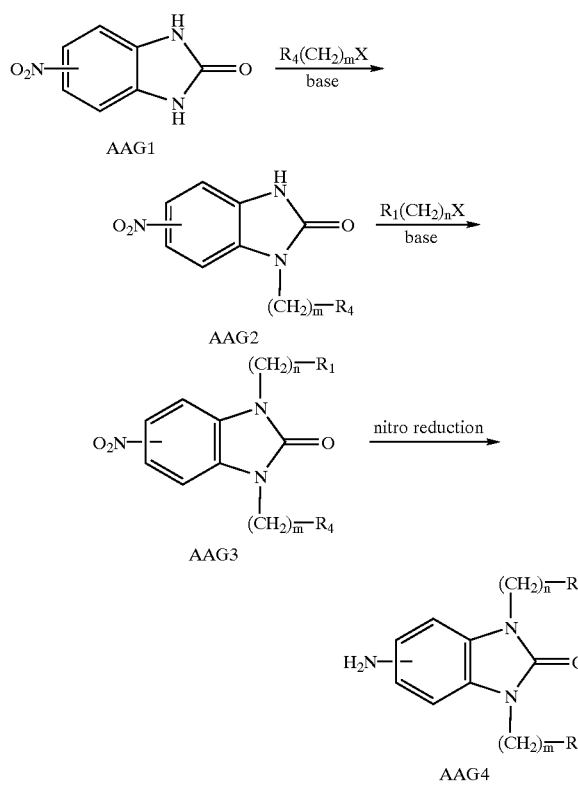

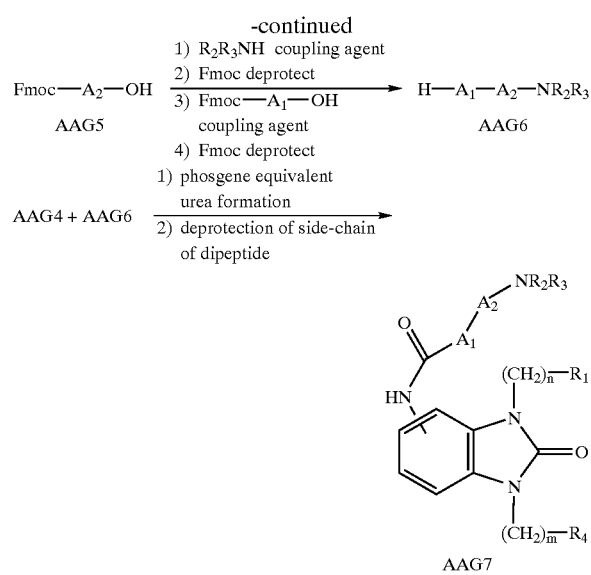

As a typical example of this convergent solution-phase method, Compound 1 may be synthesized as described in Scheme AA. Thus, treatment of 5-nitrobenzimidazolone AAI with 2,6-diCl-Bn-Br in the presence of NaH in DMF afforded two regioisomers AA2a and AA3a (ca. 1:1 ratio), which were then separated by flash column. A small amount of bis-alkylated product was also obtained. The isolated AA3a was further alkylated with 2-chloroethylpyrrolidine by using NaH as a base in DMF to give the di-alkylated product, which was then subjected to nitro reduction with Me$_2$NNH$_2$/FeCl$_3$ to provide aminobenzimidazolone intermediate AA4. Coupling of N-α-Fmoc-N-γ-Boc-diaminobutyric acid (AA5) with benzyl amine in the presence of DCC and HOBt was followed by de-protection of the Fmoc group with diethylamine. The resulting intermediate was coupled with Fmoc-3,4-diF-Phe-OH using DIC/HOBt and treated with diethylamine to give dipeptide amine AA6. Urea formation between the dipeptide amine AA6 and aminobenzimidazolone intermediate AA4 in the presence of 4-nitrophenylchloroformate was followed by de-protection of the Boc group with TFA to afford the target compound 1.

In an alternative approach to the targets, the preferred intermediate AA3 could be prepared via a regioselective method. For example, reductive alkylation of 4-nitro-1,2-phenylenediamine AB1 with one equivalent of 4-fluorobenzaldehyde in the presence of sodium triacetoxyborohydride gave mono-alkylated product AB2 which was then cyclized with N,N'-disuccinimidyl carbonate in acetonitrile to give AA3c (Scheme AB). By following the same procedure as described in Scheme M, the target 6 was obtained from intermediate AA3c.

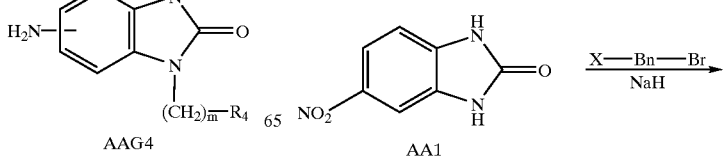

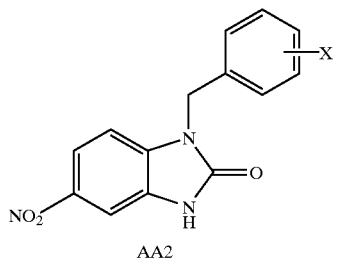
AA2
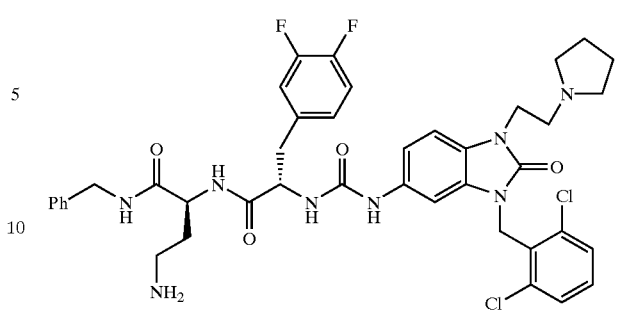
1
SCHEME AB
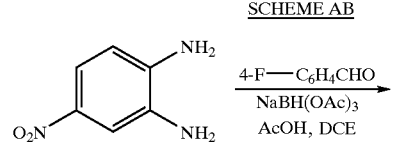
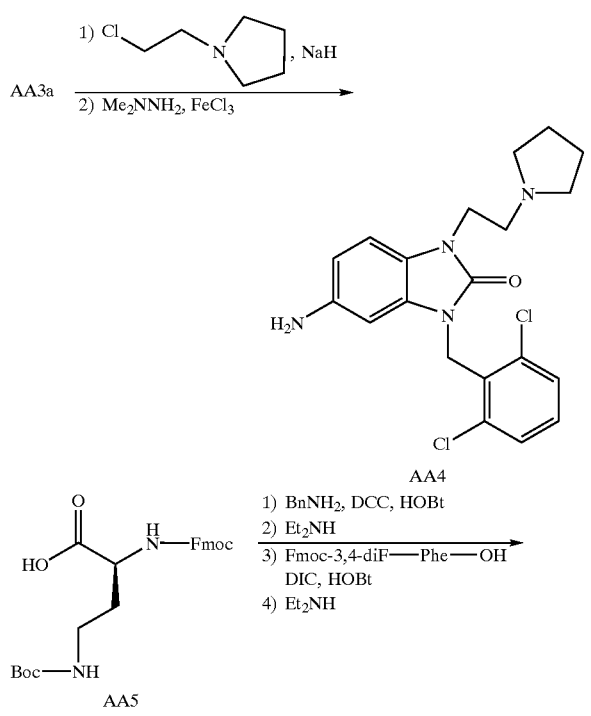
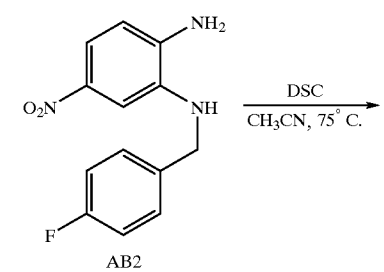
AA3c
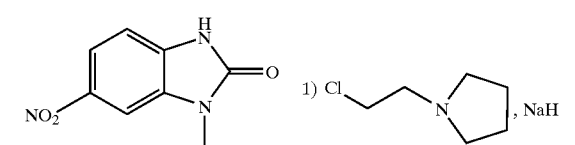
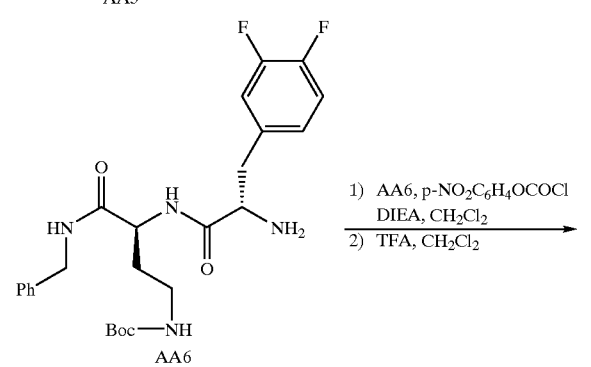
AA6
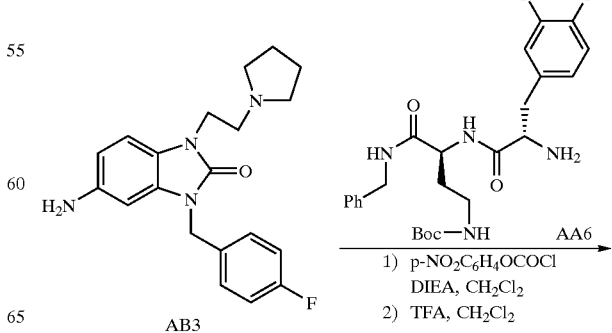

-continued

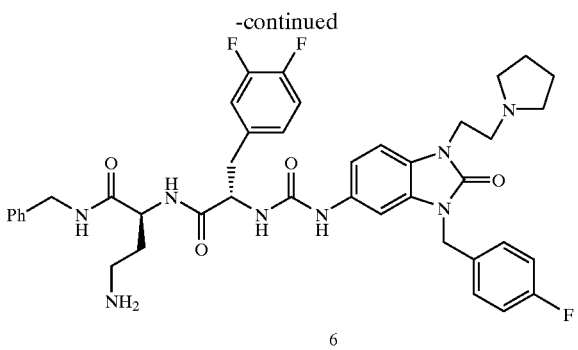

6

The side-chain amine in antagonists such as Compound 1 and Compound 8 may be converted to other functional groups such as acetamidine and guanidine by using standard procedures. For example, the acetamidine and guanidine groups can be introduced by treating the side-chain amine with S-2-naphthylmethyl thioacetimidate hydrobromide and 2-methyl-2-thiopseudourea, respectively.

The thioureidoindoles [when X is S, as in general formula (I)] may be prepared as described hereinafter. The aminobenzimidazolone substrate is reacted with thiocarbonyldiimidazole in a chlorinated solvent and then with the imidazole by-product filtered from the solution. The solution can then be concentrated to afford the N-imidazolyl-N'-benzimidazolonyl-thioamide. This intermediate is then reacted with a peptide amine in a polar, aprotic solvent with heating (from about 80° C. to about 100° C.) to afford the N-peptido-N'-benzimidazolonyl-thiourea product.

Amidobenzimidazolone targets [when p is 0 and X is O, as in general formula (I)] may be prepared from a dipeptide amine AAG6 (Scheme AAGeneric) and a benzimidazolone carboxylic acid intermediate by using standard coupling conditions such as DCC/HOBt. The required benzimidazolone carboxylic acid intermediates can be prepared by using the method as described for aminobenzimidazolone intermediate AAG4 in Scheme AAGeneric from the appropriate benzimidazolone carboxylic acid esters.

The utility of the compounds to treat PAR-1 mediated disorders (e.g., thrombotic disorders) can be determined according to the procedures described herein. The present invention therefore provides a method of treating PAR-1 mediated disorders (e.g., thrombotic disorders) in a subject in need thereof which comprises administering any of the compounds as defined herein in a quantity effective to treat PAR-1 mediated disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.03 mg/kg to about 100 mg/kg (preferred from about 0.1 mg/kg to about 30 mg/kg) of a compound of the present invention and may be given at a dosage from about 0.1 mg/kg/day to about 300 mg/kg/day (preferred from about 1 mg/kg/day to about 50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums and other pharmaceutical diluents, e.g. water, to form a solid preformulation composition containing a homogeneous mixture of a compound of the present invention or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The method of treating PAR-1 mediated disorders described in the present invention may also be carried out using a pharmaceutical composition comprising any of the compounds as defined herein and a pharmaceutically acceptable carrier. The pharmaceutical composition may contain between about 0.01 mg to about 100 mg, preferably from about 5 to about 50 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of PAR-1 mediated disorders is required.

The daily dosage of the products may be varied over a wide range from about 0.01 mg to about 1,000 mg per adult human per day. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250 and 500 mg of the active ingredient for the symptomatic adjustment of the dosage to the patient to be treated. An effective amount of the drug is ordinarily supplied at a dosage level of from about 0.01 mg/kg to about 100 mg/kg of body weight per day. Preferably, the range is from about 0.03 mg/kg to about 10 mg/kg of body weight per day. The compounds may be administered on a regimen of about 1 time per day to about 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Biology

The compounds of the present invention are thrombin receptor (PAR-1) antagonists. The compounds interrupt platelet activation induced by thrombin's proteolytic cleavage of its platelet surface receptor, and thereby inhibit platelet aggregation. Such compounds are, therefore, useful in treating platelet-mediated thrombotic disorders (e.g., arterial and venous thrombosis, acute myocardial infarction, reocclusion following thrombolytic therapy and angioplasty, and a variety of vaso-occlusive disorders) and other PAR-1 mediated disorders.

In Vitro Thrombin Receptor Binding Assay

CHRF membranes (Jones, *Biochim. Biophys. Acta* 1992, 1136, 272) are thawed from −70° C., centrifuged at maximum speed for 5 min, washed twice with binding buffer (50 mM HEPES containing 5 mM $MgCl_2$ and 0.1% BSA), and re-suspended in binding buffer (25 µg/100 mL). 100 µL of membranes are added to the 24-Wallac plates and delivered to the Tomtech apparatus. In a typical experiment, 6 µL of samples (from a 125 µg/mL intermediary plate, 20% DMSO) and 44 µL buffer are delivered to the plates (final. conc. of compounds is 3.7 µg/mL, 0.6% DMSO). Similarly, 6 µL 20% DMSO and 44 µL buffer are delivered to both column 1 (NSB) and column 12 (TB). 10 µL Ser-pFPhe-Har-Leu-Har-Lys-Tyr-$NH_2$, SEQ ID NO 1, (721-40; 500 µM in deionized water) is added to column 1. 50 µL tritiated 721-40 (specific activity 46 Ci/mmol) is added to all the wells. The plates are mixed well for 20 seconds, incubated for 30 min, and then harvested with 10 mM HEPES/138 mM NaCl using the Skatron harvester. The filters (GF/C Brandel FPXLR 296) are presoaked 3 h in 0.5% polyethylenimine in HEPES/0.1M N-acetylglucosamine) are set in saran wrap and dried for 3 min in the microwave, and placed in sample bags (Wallac 1450-432). 4.5 mL scintillation fluid (Wallac, Betaplate Scint 1205-440) is added. The bags are sealed, placed in filter cassettes (Wallac 1450-104), and analyzed on the microbeta counter.

In Vitro Inhibition of Thrombin-induced Gel-filtered Platelet Aggregation Assay

The percentage of platelet aggregation is calculated as an increase in light transmission of compound-treated platelet concentrate vs. control-treated platelet concentrate. Human blood is obtained from drug free, normal donors in tubes containing 0.13M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to $2 \times 10^7$ platelets per sample. The following constituents are added to a siliconized cuvette: concentrated platelet filtrate and Tyrode's buffer (0.14M NaCl, 0.0027M KCl, 0.012M $NaHCO_3$, 0.76 mM $Na_2HPO_4$, 0.0055M glucose, 2 mg/mL BSA and 5.0 mM HEPES @ pH 7.4) in an amount equal to 350 µL, 50 µL of 20 mM calcium and 50 µL of the test compound. Aggregation is monitored in a BIODATA aggregometer for the 3 min following the addition of agonist (thrombin 50 µL of 1 unit/mL).

Tables 1 and 2 show the biological activity of the compounds of the present invention. Tables 1 and 2 contain $IC_{50}$ values (µM) of the compounds against platelet aggregation stimulated by thrombin and $IC_{50}$ values (µM) in a thrombin receptor (PAR-1) binding assay.

EXAMPLES

General Procedures: Protected amino acids were purchased from Novabiochem, Bachem Bioscience, Advanced ChemTech or SyntheTech. All other chemicals were obtained from commercial suppliers and used without further purification. $^1H$ and $^{13}C$ NMR spectra were recorded on a Bruker AC 300B (300 MHz proton)or a Bruker AM400 (400 MHz proton) spectrometer with $Me_4Si$ as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-µm silica gel plates. Preparative TLC was performed with Analtech 1000-µm silica gel GF plates. Flash column chromatography was conducted with flash column silica gel (40–63 µm) and column chromatography was conducted with standard silica gel. HPLC separations were carried out on three Waters PrepPak® Cartridges (25×100 mm, Bondapak® C18, 15–20 µm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

In the examples and throughout this application, the following abbreviations have the meanings recited hereinafter:

| | |
|---|---|
| Ac | Acetyl |
| ACN | Acetonitrile |
| Bn | Benzyl |
| Boc | t-Butoxycarbonyl |
| DCC | 1,3-Dicyclohexylcarbodiimide |
| DCM | Dichloromethane |
| DIC | Diisopropylcarbodiimide |
| DIEA | Diisopropylethylamine |
| DMAP | 4-Dimethylaminopyridine |
| DMF | N,N-Dimethylformamide |
| Et | Ethyl |
| Fmoc | 9-Fluorenylmethoxycarbonyl |
| h | Hour |
| HBTU | 2-(1H-Benzotriazole-1-yl)-1,1,3,3-tetramethyluronium hexafluorophosphate |
| HOAc | Acetic acid |
| HOBT | Hydroxybenzotriazole |
| Me | Methyl |
| min | Minute |
| rt | room temperature |
| THF | Tetrahydrofuran |
| TFA | Trifluoroacetic acid |

Example 1

Synthesis of Compound 1 (Scheme AA)

Benzenepropanamide, N-[(1S)-3-Amino-1-[[(phenylmethyl)amino]carbonyl]propyl]-α-[[[3-(2,6-dichlorophenyl)methyl]-2,3-dihydro-2-oxo-1-[2-(1-pyrrolidinyl)ethyl]-1H-benzimidazol-5-yl]amino]carbonyl]amino]-3,4-difluoro-, (αS)- (1)

5-Nitroimidazolone AA1 (1.44 g, 8.04 mm) in dry DMF (20 mL) under argon was cooled to about 0° C. and 75%

NaH oil dispersion (0.284 g, 8.86 mm) was added portionwise and stirred for about 5 min. 2,6-Dichlorobenzylbromide (1.92 g, 8.0 mm) dissolved in dry DMF (20 mL) was added over about 5 min and the reaction was stirred at about 0° C. for about 30 min and then at about rt for about 3 h. The solution was added slowly to vigorously stirring water (700 mL) and after about 1 h, a white solid was filtered (2.38 g) that contained a mixture of AA2a and AA3a (ca. 1:1 ratio). A portion (1.5 g) was purified by flash column chromatography using DCM:ethyl acetate (2:1) to give pure AA2a and AA3a. A sample of AA3a (105 mg, 0.30 mm) was dissolved in dry DMF (6 mL), 75% NaH (30 mg, 0.94 mm) was added and the mixture was stirred for about several min at about rt. 2-chloroethylpyrrolidine hydrochloride (103 mg, 0.60 mm) was added and the mixture was stirred at about 50° C. for about 2 h. The reaction was cooled and partitioned between chloroform:2-propanol (10:1) and water; the organic solution was washed twice with water, once with brine, dried ($K_2CO_3$) and evaporated in vacuo to a light yellow solid (130 mg). This solid was dissolved in MeOH (8.0 mL) and ferric chloride hexahydrate (30 mg, 0.11 mm), charcoal (60 mg, 5 mm) and 1,1 dimethyl hydrazine (1.5 g, 25 mm) were added and the reaction was refluxed for about 3 h. The solution was cooled to about rt, filtered through dicalite and the filtrate was evaporated in vacuo to a clear oil. The oil was dissolved in 1N HCl (25 mL) and washed twice with ethyl ether. The acid was made alkaline with dilute NaOH and extracted with DCM, which was washed twice with sodium bicarbonate solution, once with brine, dried ($K_2CO_3$) and evaporated in vacuo to give solid AA4 (100 mg). Fmoc-α-N-Boc-γ-N-diaminobutyric acid AA5 (10.8 g, 24.5 mmol) was stirred in ACN (300 mL) under argon as HOBT (3.75 g, 24.4 mmol) was added, followed by benzylamine (2.6 g, 24.3 mmol). DCC (10.4 g, 48.7 mmol) was also then added and the reaction was stirred at about rt for about 3 h, whereupon a white solid was filtered and washed with cold ACN (14.4 g). The solid was stirred in ACN (500 mL) containing diethyl amine (25 mL) for about 2 h and a small quantity of solid was filtered; the filtrate was evaporated in vacuo to an oil, which was triturated three times with hexane (400 mL each) to white solid. The solid was dissolved in ACN (400 mL), then HOBT (2.9 g, 19.1 mm) and Fmoc-3,4 difluorophenylalanine (8.1 g, 19.1 mmol) were added, followed by DIC (4.81 g, 38.2 mmol) and stirred at about rt for about 16 h. The reaction was cooled in an ice bath and a white solid was filtered then washed with cold ACN. The solid was stirred in ACN (350 mL) containing diethylamine (35 mL) for about 5 h and evaporated in vacuo to a white solid. The solid was triturated three times with hexane, dissolved in chloroform (250 mL), dried ($Na_2SO_4$) and evaporated in vacuo to a white solid AA6 (8.0 g). 4-Nitrophenyl chloroformate (20 mg, 0.10 mm) in DCM (5 mL) was cooled to about −20° C. and AA4 (40 mg, 0.10 mm) and diisopropylethylamine (13 mg, 0.10 mm) in DCM (1.5 mL) were added and stirred for about 30 min. The amine AA6 (50 mg, 0.10 mm) and diisopropylethylamine (13 mg, 0.10 mm) in DCM (2.0 mL) were added to the solution at about −20° C. and stirred at about −20° C. for about 30 min. The mixture was then allowed to come to about rt, whereupon the reaction was stirred for about another 16 h. A light yellow solid was filtered (45 mg) and then stirred into DCM (7 mL) containing anisole (10 mg) as TFA (3.0 mL) was added under argon. The reaction was stirred at about rt for about 1.5 h and then evaporated in vacuo to an oil, which was triturated three times with ethyl ether to give Compound 1, a white solid, as its trifluoroacetate salt. $^1$H NMR ($CD_3OD$) δ 1.9–2.2 (m, 6H), 2.9–3.1 (m, 3H), 3.1–3.3 (m, 4H), 3.6 (dd, 2H), 3.8 (m, 2H), 4.25 (dd, 2H), 4.35 (s, 2H), 4.45 (dd, 2H), 5.32 (s, 2H), 7.0–7.5 (m, aromatics). ES-MS m/z 821 (MH$^+$). FAB-HRMS calcd for $C_{41}H_{44}Cl_2F_2N_8O_4$+ H$^+$: 821.2909, found 821.2918.

Example 2

Synthesis of Compound 6 (Scheme AB)

Benzenepropanamide, N-[(1S)-3-Amino-1-[[(phenylmethyl)amino]carbonyl]propyl]-α-[[[[3-(4-fluorophenyl)methyl]-2,3-dihydro-2-oxo-1-[2-(1-pyrrolidinyl)ethyl]-1H-benzimidazol-5-yl]amino] carbonyl]amino]-3,4-difluoro-, (αS)- (6)

4-Nitro-1,2-phenylene diamine (AB1, 2.00 g, 13.0 mmml) was suspended in DCE (100 mL) followed by the addition of 4-fluorobenzaldehyde (1.39 mL, 13.0 mmol), acetic acid (0.74 mL, 13.0 mmol), and sodium triacetoxyborohydride (5.51 g, 26.0 mmol). Reaction was stirred at ambient temperature for 24 h. Additional sodium triacetoxyborohydride (5.51 g, 26.0 mm) was added and the reaction was stirred at ambient temperature for 24 h. The reaction mixture was diluted with EtOAc (175 mL), washed with $H_2O$ (2×50 mL), brine (50 mL), dried ($Na_2SO_4$), and evaporated in vacuo to give a solid. The crude product was purified by column chromatography (silica gel, 20% EtOAc/80% Hexane to 40% EtOAc/60% Hexane) to afford AB2 (1.42 g, 42%). To a solution of AB2 (1.39 g, 5.3 mmol) in acetonitrile (80 mL) was added N,N'-disuccinimidyl carbomate (1.36 g, 5.3 mmol) in acetonitrile (80 mL) and the mixture was stirred at 75° C. After 24 h, additional N,N'-disuccinimidyl carbonate (1.36 g, 5.3 mmol) was added and the reaction mixture stirred at 75° C. for another 24 h. The reaction was still not complete and additional N,N'-disuccinimidyl carbonate (1.36 g, 5.3 mm) was added. The stirring was continued at 75° C. for 4 h, and then the reaction mixture was evaporated in vacuo to give a solid. The crude product was purified by column chromatography (silica gel-30% EtOAc/70% Hexane to 50% EtOAc/50% Hexane) to afford AA3c (0.95 g, 62%). $^1$H NMR (DMSO) δ 5.13 (s, CH$_2$), 7.16–7.21 (m, 3H, H-11, H-13, and H-3), 7.39–7.44 (m, 2H, H-10 and H-13, 7.97–8.01 (m, 2H, H-4 and H-5), 11.76 (s, NH). To a solution of AA3c (0.50 g, 1.7 mmol) in dry DMF (24 ml) was added 60% NaH (0.20 g, 5.1 mm) and the mixture was stirred at rt for several min. 2-Chloroethylpyrrolidine hydrochloride (0.57 g, 3.4 mmol) was added and the mixture was stirred at about 50° C. overnight. The reaction was cooled to rt and additional 60% NaH (32.0 mg, 0.85 mmol) and 2-chloroethylpyrrolidine hydrochloride (57.8 mg, 0.34 mmol) was added and the mixture was stirred at about 50° C. for 5 h. The reaction was cooled and partitioned between chloroform:2-propanol (10:1) and water; the organic solution was washed twice with water, twice with brine, dried ($K_2CO_3$) and evaporated in vacuo to give a light yellow solid (0.72 g). The solid (0.70 g, 1.8 mmol) was dissolved in MeOH (50 mL) and ferric chloride hexahydrate (0.19 g, 0.70 mmol), charcoal, (0.39 g) and 1,1-dimethyl hydrazine (12.2 mL, 160 mmol) were added and the reaction was refluxed for 2 h. The solution was cooled to rt, filtered through celite and the filtrate was evaporated in vacuo to give an oil. The oil was dissolved in 1N HCl (150 mL) and washed twice with ether. The acid was basified with aqueous NaOH, extracted with DCM, which was washed twice with sodium bicarbonate solution, twice with brine, dried (K$_2$CO$_2$) and evaporated in vacuo to give solid AB3 (0.39 g). 4-Nitrophenyl chloroformate (0.028 g, 0.14 mmol) in DCM (5 mL) was cooled to about −20 °C. and AB3 (50 mg, 0.14 mmol) and diisopropylethylamine (18 mg, 0.14 mmol) in DCM (1.5 mL) were added and stirred for 2 h. The amine AA6 (0.079 g, 0.14 mmol) and diisopropylethylamine (18 mg, 0.14 mmol) in DCM (2.0 mL) were added to the solution at about −20° C. and stirred at about −20° C. for 1 h. The mixture was then allowed to warm up to rt, whereupon the reaction was stirred for about 18 h. A light yellow solid was collected by filtration and then treated with 30% TFA/DCM/1% anisole (8 mL) under N$_2$. The reaction was stirred at rt for 1 h and was then blown down with N$_2$ to an oil, which was triturated four times with ethyl ether to give compound 6, a white solid, as its trifluoroacetate salt. $^1$H NMR (CD$_3$OD) δ 1.95–2.20 (m, 6H), 2.96–3.61 (m, 11H), 4.29–4.33 (m, 4H), 4.47 (dd, 2H), 5.01 (d, 2H), 6.96–7.36 (m, aromatics). ES-MS m/z 771 (MH$^+$).

Example 3

As a specific embodiment of an oral composition, 100 mg of the Compound 1 of Example 1 is formulated with sufficient finely divided lactose to provide a total amount of about 580 mg to about 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A compound of the following formula (I):

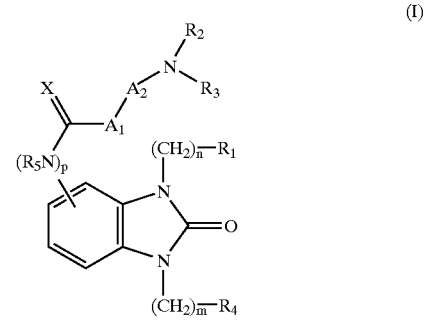

wherein:
A$_1$ and A$_2$ are each independently a D- or L-amino acid selected from the group consisting of alanine, β-alanine, arginine, homoarginine, cyclohexylalanine, citrulline, cysteine (optionally substituted with C$_1$–C$_4$ alkyl, aryl, or arC$_1$–C$_4$ alkyl), 2,4-diaminobutyric acid (optionally substituted with acyl, C$_1$–C$_4$ alkyl, aroyl, amidino, or MeC(NH)—), 2,3 diaminopropionic acid (optionally substituted with acyl, C$_1$–C$_4$ alkyl, aroyl, amidino, or MeC(NH)—), glutamine, glycine, indanylglycine, lysine (optionally substituted with acyl, C$_1$–C$_4$ alkyl, aroyl, or MeC(NH)—), valine, methionine, proline, serine (optionally substituted with C$_1$–C$_4$ alkyl, aryl, or arC$_1$–C$_4$ alkyl), homoserine (optionally substituted with C$_1$–C$_4$ alkyl, aryl, or arC$_1$–C$_4$ alkyl), tetrahydroisoquinoline-3-COOH, threonine (optionally substituted with C$_1$–C$_4$ alkyl,

SEQUENCE LISTING

<160> NUMBER OF SEQ ID NOS: 1

<210> SEQ ID NO 1
<211> LENGTH: 7
<212> TYPE: PRT
<213> ORGANISM: Artificial
<220> FEATURE:
<223> OTHER INFORMATION: Sequence is an artificial antagonist for PAR1 receptor
<220> FEATURE:
<221> NAME/KEY: MISC_FEATURE
<222> LOCATION: (2)..(2)
<223> OTHER INFORMATION: X is para-fluorophenylalanine
<220> FEATURE:
<221> NAME/KEY: MISC_FEATURE
<222> LOCATION: (3)..(3)
<223> OTHER INFORMATION: X is homoarginine
<220> FEATURE:
<221> NAME/KEY: MISC_FEATURE
<222> LOCATION: (5)..(5)
<223> OTHER INFORMATION: X is homoarginine

<400> SEQUENCE: 1

Ser Xaa Xaa Leu Xaa Lys Tyr
1               5 aryl, or arC$_1$–C$_4$ alkyl), ornithine (optionally substituted with acyl, C$_1$–C$_4$ alkyl, aroyl, or MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein one or more of the substituents on the aromatic amino acid are independently selected from the group consisting of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, and nitro;

$R_1$ is selected from the group consisting of amino, $C_1$–$C_8$ alkylamino, $C_1$–$C_8$ dialkylamino, arylamino, ar$C_1$–$C_8$ alkylamino, $C_3$–$C_8$ cycloalkylamino, heteroalkyl$C_1$–$C_8$ alkylamino, heteroalkyl$C_1$–$C_8$ alkyl-N-methylamino, $C_1$–$C_8$ dialkylamino$C_1$–$C_8$ alkylamino, —N($C_1$–$C_8$alkyl)—$C_1$–$C_8$ alkyl-N($C_1$–$C_8$alkyl)$_2$, N($C_1$–$C_8$ alkyl) ($C_1$–$C_8$ alkenyl), —N($C_1$–$C_8$alkyl) ($C_3$–$C_8$cycloalkyl), heteroalkyl and substituted heteroalkyl wherein the substituent on the heteroalkyl is selected from the group consisting of oxo, amino, $C_1$–$C_8$ alkoxy$C_1$–$C_8$ alkyl, $C_1$–$C_8$ alkylamino and $C_1$–$C_8$ dialkylamino;

$R_2$ and $R_3$ are each independently selected from the group consisting of hydrogen, $C_1$–$C_8$ alkyl, $C_3$–$C_8$ cycloalkyl, $C_3$–$C_8$ cycloalkyl$C_1$–$C_8$ alkyl, aryl, heteroalkyl, substituted heteroalkyl (wherein the substituent on the heteroalkyl is one or more substituents independently selected from the group consisting of $C_1$–$C_8$ alkoxycarbonyl, $C_1$–$C_8$ alkyl, and $C_1$–$C_4$ alkylcarbonyl), heteroalkyl$C_1$–$C_8$ alkyl, indanyl, acetamidino$C_1$–$C_8$ alkyl, amino$C_1$–$C_8$ alkyl, $C_1$–$C_8$ alkylamino$C_1$–$C_8$ alkyl, $C_1$–$C_8$ dialkylamino$C_1$–$C_8$ alkyl, unsubstituted or substituted heteroaryl$C_1$–$C_8$ alkyl and unsubstituted or substituted ar$C_1$–$C_8$ alkyl, wherein the substituent on the aralkyl or heteroaralkyl group is one or more substituents independently selected from the group consisting of halogen, nitro, amino, $C_1$–$C_8$ alkyl, $C_1$–$C_8$ alkoxy, hydroxy, cyano, $C_1$–$C_4$ alkylcarbonyl, $C_1$–$C_8$ alkoxycarbonyl, hydroxy$C_1$–$C_8$ alkyl and aminosulfonyl; or $R_2$ and $R_3$, together with the nitrogen to which they are attached, alternatively form an unsubstituted or substituted heteroalkyl group selected from the group consisting of piperidinyl, piperazinyl, morpholinyl and pyrrolidinyl, wherein the substituent is one or more substituents independently selected from the group consisting of $C_1$–$C_8$alkyl $C_1$–$C_8$ alkoxycarbonyl and $C_1$–$C_4$ alkylcarbonyl;

$R_4$ is selected from the group consisting of unsubstituted or substituted aryl, ar$C_1$–$C_8$ alkyl, $C_3$–$C_8$ cycloalkyl, and heteroaryl, where one or more of the substituents on the aryl, ar$C_1$–$C_8$alkyl, cycloalkyl or heteroaryl group are independently selected from the group consisting of halogen, nitro, amino, cyano, hydroxyalkyl, $C_1$–$C_8$ alkyl, $C_1$–$C_8$ alkoxy, hydroxy, $C_1$–$C_4$ alkylcarbonyl, $C_1$–$C_8$ alkoxycarbonyl, fluorinated $C_1$–$C_4$ alkyl, fluorinated $C_1$–$C_4$ alkoxy, and $C_1$–$C_4$ alkylsulfonyl;

$R_5$ is selected from the group consisting of hydrogen and $C_1$–$C_8$ alkyl;

X is oxygen or sulfur;

m is an integer selected from the group consisting of 0, 1, 2 and 3;

n is an integer selected from the group consisting of 2 and 3; and p is an integer selected from the group consisting of 0 and 1;

or a pharmaceutically acceptable salt thereof.

2. The compound of claim 1, wherein:

$A_1$ and $A_2$ are each independently an L-amino acid selected from the group consisting of alanine, β-alanine, arginine, homoarginine, cyclohexylalanine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3 diaminopropionic acid (optionally substituted with acyl, $C_1$–$C_4$ alkyl, aroyl, amidino, or MeC(NH)—), glutamine, glycine, indanylglycine, lysine (optionally substituted with acyl, $C_1$–$C_4$ alkyl, aroyl, or MeC(NH)—), valine, methionine, proline, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), tetrahydroisoquinoline-3-COOH, threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, or MeC(NH)—), and an unsubstituted or substituted aromatic amino acid selected from the group consisting of phenylalanine, heteroarylalanine, naphthylalanine, homophenylalanine, histidine, tryptophan, tyrosine, arylglycine, heteroarylglycine, aryl-β-alanine, and heteroaryl-β-alanine wherein one or more of the substituents on the aromatic amino acid are independently selected from the group consisting of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, and nitro;

$R_1$ is selected from the group consisting of amino, $C_1$–$C_6$ alkylamino, $C_1$–$C_6$ dialkylamino, arylamino, ar$C_1$–$C_6$ alkylamino, heteroalkyl$C_1$–$C_6$ alkylamino, —N($C_1$–$C_6$alkyl)—$C_1$–$C_6$ alkyl-N($C_1$–$C_6$alkyl)$_2$, heteroalkyl and substituted heteroalkyl wherein the substituent on the heteroalkyl is selected from the group consisting of oxo, amino, $C_1$–$C_6$alkoxy$C_1$–$C_6$ alkyl, $C_1$–$C_6$ alkylamino and $C_1$–$C_6$ dialkylamino;

$R_2$ is selected from the group consisting of hydrogen and $C_1$–$C_6$ alkyl;

$R_3$ is selected from the group consisting of $C_1$–$C_8$alkyl, $C_3$–$C_6$ cycloalkyl, $C_3$–$C_6$ cycloalkyl$C_1$–$C_6$ alkyl, aryl, heteroaryl$C_1$–$C_6$ alkyl, substituted heteroaryl$C_1$–$C_6$alkyl wherein the substituent is $C_1$–$C_4$ alkyl, heteroalkyl, heteroalkyl$C_1$–$C_6$ alkyl, indanyl, acetamidino$C_1$–$C_6$ alkyl, amino$C_1$–$C_6$ alkyl, $C_1$–$C_6$alkylamino$C_1$–$C_6$ alkyl, $C_1$–$C_6$ dialkylamino$C_1$–$C_6$ alkyl, ar$C_1$–$C_8$alkyl, substituted ar$C_1$–$C_8$ alkyl wherein the substituent on the aralkyl group is one to five substituents independently selected from the group consisting of halogen, nitro, amino, $C_1$–$C_6$ alkyl, $C_1$–$C_6$ alkoxy, $C_1$–$C_6$ alkoxycarbonyl, hydroxyalkyl and aminosulfonyl;

$R_2$ and $R_3$, together with the nitrogen to which they are attached, alternatively form an unsubstituted or substituted heteroalkyl group selected from the group consisting of piperidinyl, piperazinyl and pyrrolidinyl, wherein the substituent is independently one or two substituents selected from $C_1$–$C_6$ alkyl;

$R_4$ is selected from the group consisting of unsubstituted or substituted aryl, ar$C_1$–$C_6$ alkyl, $C_3$–$C_6$ cycloalkyl and heteroaryl, where one to three of the substituents on the aryl, aralkyl, cycloalkyl or heteroaryl group are independently selected from substituents selected from the group consisting of halogen, cyano, $C_1$–$C_4$ alkyl, $C_1$–$C_4$ alkoxy, $C_1$–$C_4$alkoxycarbonyl, fluorinated $C_1$–$C_4$ alkyl, fluorinated $C_1$–$C_4$ alkoxy and $C_1$–$C_4$alkylsulfonyl;

$R_5$ is hydrogen;

X is oxygen; and p is 1;

or a pharmaceutically acceptable salt thereof.

3. The compound of claim 2, wherein:

$A_1$ is an L-amino acid selected from the group consisting of alanine, arginine, cyclohexylalanine, glycine, proline, tetrahydroisoquinoline-3-COOH, and an unsubstituted or substituted aromatic amino acid selected from the group consisting of phenylalanine, naphthylalanine, homophenylalanine, and O-methyl tyrosine, wherein from one to five of the substituents on the aromatic amino acid are independently selected from the group consisting of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, and nitro;

$A_2$ is an L-amino acid selected from the group consisting of alanine, β-alanine, arginine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, lysine (optionally substituted with acyl, $C_1$–$C_4$ alkyl, aroyl, or MeC(NH)—), valine, methionine, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, or MeC(NH)—), and an unsubstituted or substituted aromatic amino acid selected from the group consisting of phenylalanine, heteroarylalanine, and histidine, wherein one to five of the substituents on the aromatic amino acid are independently selected from the group consisting of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, and nitro;

$R_2$ is selected from the group consisting of hydrogen and $C_1$–$C_4$ alkyl; and m is 1 and n is 2;

or a pharmaceutically acceptable salt thereof.

4. The compound of claim 3, wherein:

$A_1$ is an L-amino acid selected from the group consisting of alanine, arginine, cyclohexylalanine, glycine, proline, and an unsubstituted or substituted aromatic amino acid selected from the group consisting of phenylalanine, naphthylalanine, homophenylalanine, and O-methyl tyrosine, wherein the substituents on the aromatic amino acid are independently one to two substituents selected from the group consisting of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, and nitro;

$A_2$ is an L-amino acid selected from the group consisting of alanine, β-alanine, arginine, citrulline, cysteine (optionally substituted with $C_1$–$C_4$ alkyl, aryl, or ar$C_1$–$C_4$ alkyl), 2,4-diaminobutyric acid (optionally substituted with acyl, $C_1$–$C_4$ alkyl, aroyl, amidino, or MeC(NH)—), 2,3-diaminopropionic acid (optionally substituted with acyl, $C_1$–$C_4$ alkyl, aroyl, amidino, or MeC(NH)—), glutamine, glycine, lysine (optionally substituted with acyl, $C_1$–$C_4$ alkyl, aroyl, or MeC(NH)—), valine, methionine, serine (optionally substituted with $C_1$–$C_4$ alkyl, aryl, or ar$C_1$–$C_4$ alkyl), homoserine (optionally substituted with $C_1$–$C_4$ alkyl, aryl, or ar$C_1$–$C_4$ alkyl), threonine (optionally substituted with $C_1$–$C_4$ alkyl, aryl, or ar$C_1$–$C_4$ alkyl), ornithine (optionally substituted with acyl, $C_1$–$C_4$ alkyl, aroyl, or MeC(NH)—), and an unsubstituted or substituted aromatic amino acid selected from the group consisting of phenylalanine, heteroarylalanine, and histidine, wherein the substituents on the aromatic amino acid are independently one to two substituents selected from the group consisting of halogen, $C_1$–$C_4$ alkyl, $C_1$–$C_4$ alkoxy, hydroxy, $C_1$–$C_4$ alkoxycarbonyl, amino, amidino, guanidino, fluorinated $C_1$–$C_4$ alkyl, fluorinated $C_1$–$C_4$ alkoxy, $C_1$–$C_4$ alkylsulfonyl, $C_1$–$C_4$ alkylcarbonyl, cyano, aryl, heteroaryl, ar$C_1$–$C_4$ alkyl, $C_2$–$C_4$ alkenyl, alkynyl, and nitro;

$R_1$ is selected from the group consisting of dimethylamino, diethylamino, di-(n-propyl)amino,

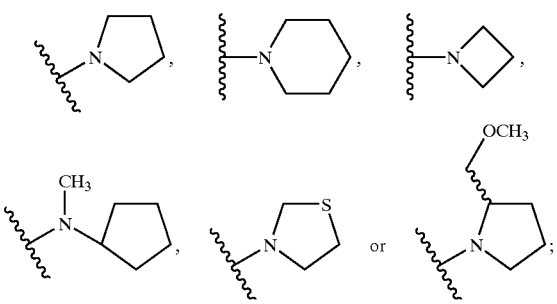

$R_2$ is selected from the group consisting of hydrogen, methyl and ethyl;

$R_3$ is selected from the group consisting of 2-indanyl, phenyl, cyclohexylmethyl, cyclopentyl, pyridylmethyl, furanylmethyl, 2-(4-methyl-furanyl)methyl, thienylmethyl, diphenylmethyl, 4-imidazolylethyl, 2-(4-N-methyl)imidazolylethyl, n-octyl, phenyl-n-propyl, aminoethyl, aminopropyl, amino-n-pentyl, dimethylaminoethyl, 4-aminophenylsulfonylaminomethyl, acetamidinylethyl, 2-N-pyrrolidinylethyl, N-ethoxycarbonylpiperidinyl, unsubstituted or substituted phenylethyl and unsubstituted or substituted benzyl wherein the substituents on the phenylethyl or benzyl are independently one or two substituents selected from the group consisting of methyl, fluorine, chlorine, nitro, methoxy, methoxycarbonyl and hydroxymethyl; or R₂ and R₃, together with the nitrogen to which they are attached, alternatively form a heteroalkyl group selected from the group consisting of piperidinyl, and 4-(N-methyl)piperazinyl; and R₄ is selected from the group consisting of cyclohexyl, 2-naphthyl, phenylethyl, 4-fluorophenylethyl, unsubstituted phenyl and substituted phenyl, where the substituents on the phenyl are independently selected from one to two substituents selected from the group consisting of fluorine, chlorine, iodine, methyl, cyano and trifluoromethyl;

or a pharmaceutically acceptable salt thereof.

5. The compound of claim 4, wherein

R₁ is

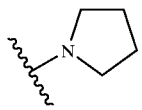

or a pharmaceutical acceptable salt thereof.

6. The compound of claim 5, wherein:
R₄ is selected from

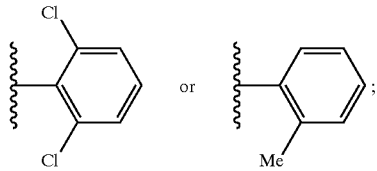

or a pharmaceutically acceptable salt thereof.

7. The compound of claim 6, wherein:
A₁ is selected from the group consisting of 3,4-Difluorophenylalanine and 4-Chlorophenylalanine;
A₂ is selected from the group consisting of 2,4-Diaminobutyric acid and 4-Pyridylalanine;
R₂ is hydrogen; and
R₃ is selected from the group consisting of benzyl and 2-aminoethyl;

or a pharmaceutically acceptable salt thereof.

8. A composition comprising a pharmaceutically acceptable carrier and a compound of claim 1.

9. A composition made by mixing a compound of claim 1 and a pharmaceutically acceptable carrier.

10. A process for making a composition comprising mixing a compound of claim 1 and a pharmaceutically acceptable carrier.

* * * * *